(12) United States Patent
Steininger et al.

(10) Patent No.: US 6,616,610 B2
(45) Date of Patent: Sep. 9, 2003

(54) METHOD FOR DETERMINATION OF THE DIRECTION OF INTRODUCTION AND FOR CONTROLLING THE INTRODUCTION PATH OF BIOPSY NEEDLES

(75) Inventors: Josef Steininger, Vöcklamarkt (AT); Arthur Gritzky, Pollham (AT)

(73) Assignee: GE Medical Systems Kretztechnik GmbH & Co. OHG, Zipf (AT)

( * ) Notice: Subject to any disclaimer, the term of this patent is extended or adjusted under 35 U.S.C. 154(b) by 0 days.

(21) Appl. No.: 10/002,095

(22) Filed: Nov. 15, 2001

(65) Prior Publication Data

US 2002/0058872 A1 May 16, 2002

(30) Foreign Application Priority Data

Nov. 16, 2000 (EP) .............................. 00890342

(51) Int. Cl.$^7$ .................................. A61B 8/00
(52) U.S. Cl. ..................... 600/443; 600/425; 600/437
(58) Field of Search .................. 600/443, 425, 600/426, 437, 439, 429, 447, 562, 462; 128/916

(56) References Cited

U.S. PATENT DOCUMENTS

| | | | |
|---|---|---|---|
| 5,967,991 A | 10/1999 | Gardineer et al. | |
| 6,019,724 A | 2/2000 | Gronningsaeter et al. | |
| 6,336,899 B1 * | 1/2002 | Yamazaki | 600/443 |
| 6,416,476 B1 * | 7/2002 | Ogasawara et al. | 600/425 |

FOREIGN PATENT DOCUMENTS

EP 0 962 785 12/1999

* cited by examiner

Primary Examiner—Marvin M. Lateef
Assistant Examiner—Ruby Jain
(74) Attorney, Agent, or Firm—Collard & Roe, P.C.

(57) ABSTRACT

With a method for determination of the direction of introduction (4) and for controlling the introduction path of biopsy needles, probes and similar in organisms (2) by using an ultrasound imaging machine, a scanning unit (1) of the ultrasound is placed onto the introduction range of the organism (2) in order to display an image (3a) according to a sectional plane (3) in which or along which the directional axis (4) of the introduction path runs and the biopsy needle or similar is controlled during its actual introduction in the corresponding image display (3a, 6). For improvement of the accuracy of introduction and for an easier procedure a larger volume range (3) of the organism (2) is scanned by using a 3D-imaging and with a contingent interim storage of the derived signals by a volume storage the sectional plane (3a) to be displayed is selected according to predeterminable criteria from the volume (3), after which selection the intended introduction path (4) is virtually displayed in this image and an e.g. prismatic or cylindrical part of the total volume is selected especially within predeterminable limits (5) being parallel to the axis of the introduction path within that image (3a), the partial volume being displayed in a 3D-image (6), in which the biopsy needle or similar can be observed during its later actual introduction.

5 Claims, 2 Drawing Sheets

Figure 1:
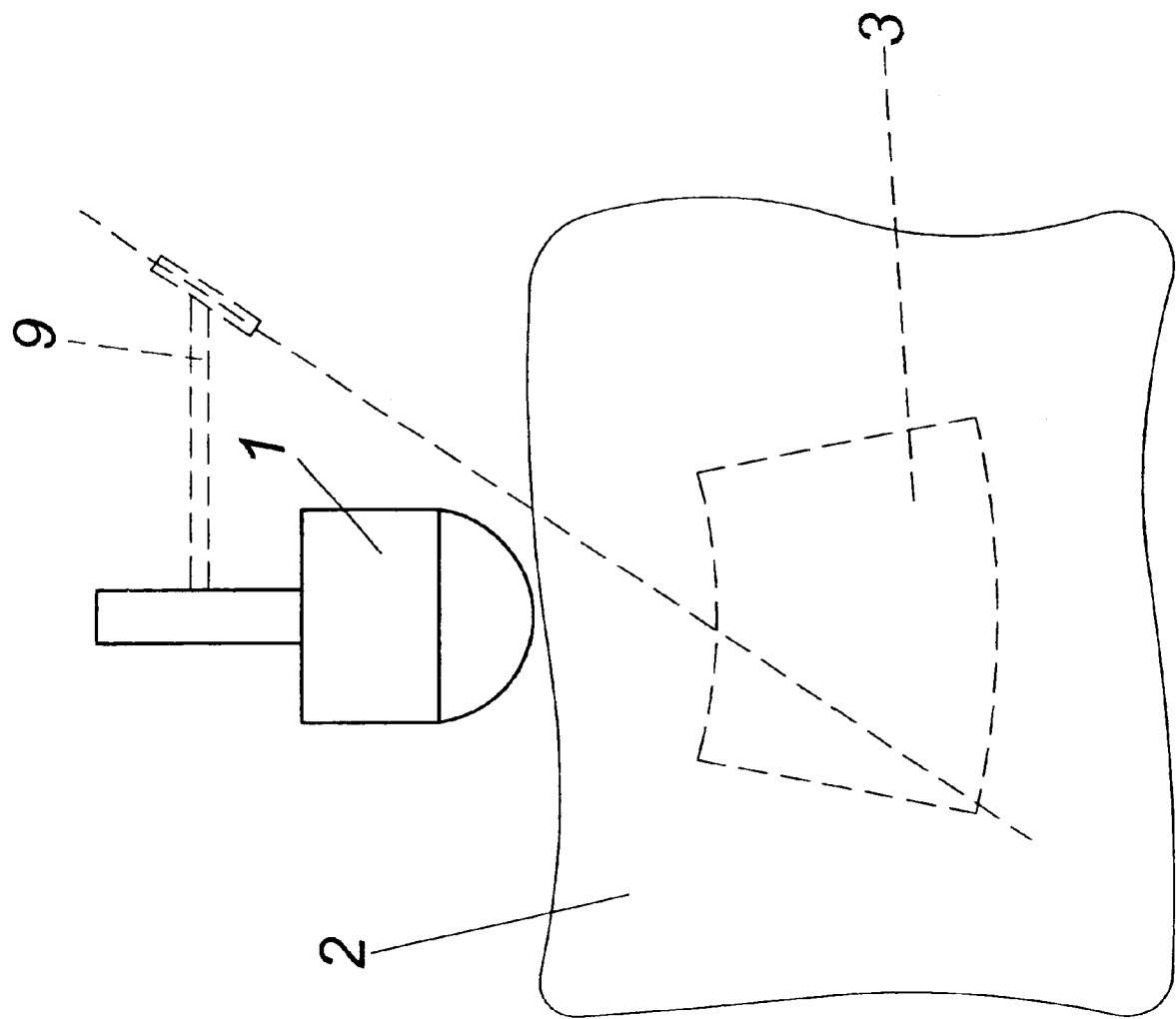

METHOD FOR DETERMINATION OF THE DIRECTION OF INTRODUCTION AND FOR CONTROLLING THE INTRODUCTION PATH OF BIOPSY NEEDLES

The present invention relates to a method according to the superordinate concept of Claim 1.

Known methods of this kind are working with relatively simple B-scan imaging units, in which the position of the displayed sectional plane is determined only by way of the contact position of the ultrasound transducer and its orientation to the organ being examined. By even only small swings of the ultrasound transducer around the horizontal or vertical axis the position of the displayed sectional plane will be varied too. In addition, when scanning living organisms, by changes of the position of either the total body, or the organ being aimed at within the body or tissue layers, corrective actions will occur within the displayed sectional plane containing the "aiming point" within the organism. It is known to provide rigidly mounted guides on the ultrasound transducer for the biopsy needle or similar to be inserted mostly at a fixed distance from the ultrasound transducer toward the sectional plane determined by that ultrasound transducer. The "ideal" direction within the sectional plane can be displayed in the B-mode image by way of a superposed auxiliary line. Also the biopsy needle or similar are being observed during the introduction. Even with a non-moving organism it is then difficult to determine whether an inexactly introduced biopsy needle leaves the displayed sectional plane in or against the aspect direction and to make appropriate corrections. In case of moving organisms, however, modifications in addition to corrections of the biopsy needle also of the contact direction, especially the contact inclination of the ultrasound transducer must be made, so that only very experienced medical doctors are able to really achieve the theoretically possible accuracy of this known method. From DE 24 25 724 A it is known to equip biopsy needles with a coating well reflecting ultrasound waves or with profiles to improve the visibility in the ultrasound image, but even this does not change anything in the above mentioned problems.

To increase the accuracy, according to AT 344 872 B two ultrasound transducers are used for a B-scan image which are connected at a distance and perpendicular to each other by a guiding device for a biopsy needle, so that the scan planes of the two ultrasound transducers intersect in a straight line within the object which is the introduction axis of the biopsy needle, determined by the biopsy needle guide. So if the aimed point in the object is on the straight line and is displayed in both images, the introduced biopsy needle will hit it with a high probability. Here also the above mentioned readjustment difficulties with moving organs or organs changing their position, the adjustment and readjustment of the ultrasound transducers becomes complicated and the examining doctor has practically no hand free to introduce the biopsy needle. Furthermore an instrument equipped this way can only be used for this single purpose and it is not always possible to fix the two ultrasound transducers to the object maintaining sufficient or good coupling quality, respectively.

It has to be mentioned here that such methods generally can be used for a great variety of purposes, i.e. for the withdrawal of fluid, tissue or other samples of organs, for punctures as well as for specific punctual treatments within organisms.

The purpose of the invention to be described herein is thus the creation of a novel method compared to those mentioned in the introduction, by which the accuracy of aiming and of introducing the biopsy needle or anything similar is improved at less critical coupling accuracy of the ultrasound transducer, ensuring also a high accuracy in case of moving organs or organs changing their position and which enables less experienced doctors to work safely with high accuracy.

The problem is solved in full by the characteristics of the method described in Claim 1. In principle, an ultrasound machine with an adequate ultrasound transducer which is subject of our own EP 0 962 785 A can be used to perform the method according to this invention. This machine is to be adapted to the conditions of the method according to the invention, especially as regarding the software, whereas in addition the mentioned sectional plane shall be displayed as a whole. The sectional plane however can be selected especially in case of machines without compulsory guiding device for the biopsy needle within the scanned total volume, whereby the adjustment is only necessary in so far as the partial volume surrounding the insertion path remains safely present within the scanned total volume. In case of ultrasound machines with compulsory guiding device, basically one will select that sectional plane for the display which lies in the target direction of the biopsy needle guide.

As in the 3D-display only the actual areas destined for the introduction of the biopsy needle and their close surroundings are made visible, this way of display is less confusing compared to a display in whole, but it offers the possibility to also visualize the curvatures of shapes within the organism being transverse to the imaged B-scan plane, which e.g. result from the surface shape or the shape of separating layers, so that the introduction point of the biopsy needle can be very accurately aimed at. Due to the 3D-display, the needle itself is well visible even when it slightly leaves the sectional image plane, thus facilitating corrections of the guidance of the needle in a way unknown before. In case of unmoving organs the limits of the selected partial volume can be set relatively close to the aiming axis. With moving organs or organs changing their position, the limits are set such that even in case of movements and without major position changes of the ultrasound transducer the aiming axis remains always within this selected partial volume. Hence in most cases a compulsory guiding device connected to the ultrasound transducer will even be unnecessary.

As already mentioned, the limiting areas of the partial volume can be selected according to different criteria. An extremely simple method is described in Sub-Claim 2.

The 3D-image display offers several further possibilities to increase the accuracy of introduction and for the precise determination of the direction of introduction. It is possible to rotate, tilt and turn round the partial image obtained by the 3D-method with methods already known, in order to examine it from all sides and to then select the direction of introduction and introduction point as wanted. Due to the customary way of image examination it also can show advantageous to align the 3D-image according to Sub-Claim 3.

The method according to the invention is not restricted to the sectional image and 3D-image technique, but can also be used with compatible methods as indicated in Claim 4. However, in case of Doppler-coded scanning a substantial decrease of the possible scan velocities will result in order to allow the Doppler evaluation. In Claim 5 a design is specified which proves excellent with a forced guidance of the instruments.

Further details and advantages of the subject of the present invention are explained in the below mentioned description of the drawings.

In the drawing the present invention is explained by an example illustration.

Figure 2:
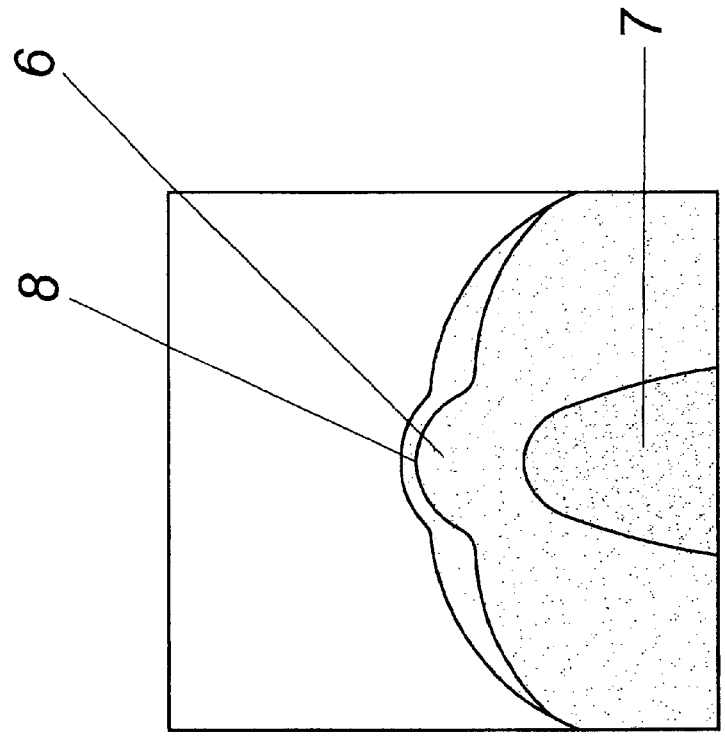
Figure 2:
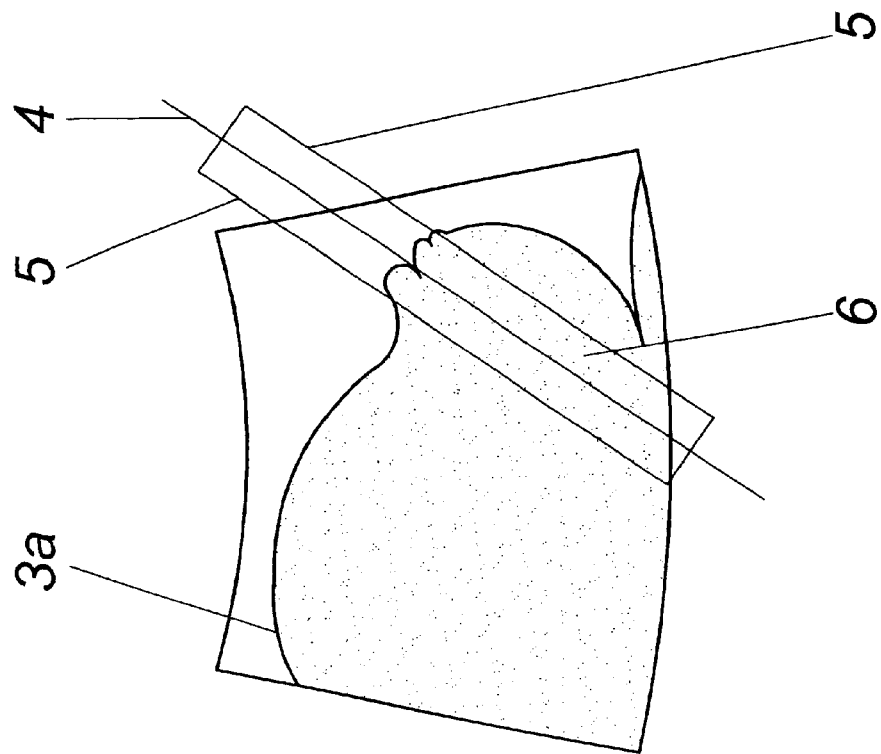

FIG. 1 shows the schematic configuration of a 3D ultrasound transducer on an object, the scanned sectional plane being indicated by broken lines, FIG. 2 shows a B-image obtained from the scanned volume as per the method of the invention and the 3D-display of the selected partial volume in the neighboring screen area.

According to FIG. 1 a 3D ultrasound transducer of a not further described ultrasound machine, but principally a 3D-image machine according to EP 0 962 785 A, is coupled to an organism 2, which it scans by the 3D volume method in a volume range obtained by moving a B-scanning plane 3 transverse to the scan area. By a corresponding derivation several B-image planes are being selected, in which the introduction range of a biopsy needle is adjusted, according to the preferred possibility of aligning the ultrasound transducer, to place it at half of the scan movement transverse to the image plane, which procedure is anyway necessary with a compulsory needle guide used. Otherwise from the further B-images that one may be selected which shows best the insertion range. Within this insertion range the auxiliary biopsy line 4 showing the course of the insertion direction as wanted resp. fixed by the needle guide is visible in the B-image 3a of FIG. 2. Also within that B-image additional lines 5 on both sides of the biopsy line 4 mark the limits of the partial volume as wanted for the 3D display mode. The thickness of the partial volume is defined by the scan movement range normal to the B-image plane. Moreover it will be defined for the 3D-image 6 of the partial volume, which is to be displayed beside of the sectional image plane 3a, in which direction to the insertion direction of the biopsy needle (to be displayed horizontal or vertical, respectively) it shall lie, and if the 3D-aspect is to be shown in a front or a rear view, the left and the right side limits being defined by the scan movement range normal to the B-image. According to FIG. 2 the image 6 shows the inclusion 7 within the organ and a prominent part into which the biopsy needle should enter are incomparably better visible than in the B-image. The biopsy needle to be introduced there will be also visible in image 6, it is however not pictured. The direction of introduction is vertical from above downward in the middle of the image.

As indicated by the drawing in broken lines in FIG. 1 it is also possible to couple permanently a forced guiding device (9) for the biopsy needle or other instrument to the scanhead (1). Hereby, in some applications, the procedure to locate the spot of the introduction and to aim in the direction of the introduction is eased.

What is claimed is:

1. A method of determining a direction of introduction and tracing an introduction path along the direction of introduction of a medical instrument into an organism, with the use of an ultrasound imaging machine suitable for 3D-imaging, comprising the steps of scanning a larger volume of the organism with a 3D-scanning Unit of the ultrasound imaging machine, generating an image of an intended introduction range in a sectional plane within which the introduction path runs, observing the introduction path in an image display of the sectional plane, the sectional plane being located by predeterminable selection criteria and the introduction path being virtually displayed, and selecting a prismatic or cylindrical part of the larger volume for display in a 3D-image in which the introduction path may be observed, the prismatic or cylindrical part of the larger volume having a main axis coaxial with the direction of introduction.

2. The method of claim 1, wherein the prismatic or cylindrical part of the larger volume has lateral limits displayed in a B-image of the sectional plane, and volume limits in front of and behind the sectional plane are determined by the 3D-image generated by the 3D-scanning unit transversely to the B-image.

3. The method of claim 2, wherein the 3D-image is displayed in an orientation extending vertically or horizonally with respect to the direction of introduction.

4. The method of claim 2, wherein in the medical instrument is vibrated during the introduction into the organism and while remaining therein to improve the visualization of B- and 3D-images additionally coded by the Doppler-method.

5. A method of determining a direction of introduction and tracing an introduction path along the direction of introduction of a medical instrument into an organism, with the use of an ultrasound imaging machine suitable for 3D-imaging, comprising the steps of scanning a larger volume of the organism with a 3D-scanning unit of the ultrasound imaging machine, determining the direction of introduction of the medical instrument with a guiding device coupled to the 3D-scanning unit, the direction of introduction being determined by the position of the guiding device relative to the 3D-scanning unit, generating a B-image of an intended introduction range in a sectional plane within which the introduction path runs, aligning the 3D-scanning unit with the guiding device coupled thereto with the sectional plane in the generated B-image, observing the introduction path in an image display of the sectional plane, the sectional plane being located by predeterminable selection criteria and the introduction path being virtually displayed, and selecting a prismatic or cylindrical part of the larger volume for display in a 3D-image in which the introduction path may be observed, the prismatic or cylindrical part of the larger volume having a main axis coaxial with the direction of introduction.

\* \* \* \* \*